United States Patent [19]

Giesecke et al.

[11] 4,377,694
[45] Mar. 22, 1983

[54] HYDROXYALKYL-1,2,4-TRIAZOLIDINE-3,5-DIONES AND A PROCESS FOR THEIR PRODUCTION

[75] Inventors: Henning Giesecke, Cologne; Rudolf Merten, Leverkusen; Ludwig Rottmaier, Odenthal, all of Fed. Rep. of Germany

[73] Assignee: Bayer Aktiengesellschaft, Leverkusen, Fed. Rep. of Germany

[21] Appl. No.: 278,648

[22] Filed: Jun. 29, 1981

[30] Foreign Application Priority Data

Jul. 21, 1980 [DE] Fed. Rep. of Germany ....... 3027551

[51] Int. Cl.³ ................. C07D 249/12; C07D 403/06; C07D 403/08; C07D 403/10
[52] U.S. Cl. ..................................... 548/264; 521/90; 528/363
[58] Field of Search ......................................... 548/264

[56] References Cited

U.S. PATENT DOCUMENTS 3,621,099 11/1971 Jacobson et al. ................... 424/269
3,737,432 6/1973 George et al. ...................... 544/222

FOREIGN PATENT DOCUMENTS 1104965 4/1961 Fed. Rep. of Germany ...... 548/246
2554866 6/1976 Fed. Rep. of Germany .
2156972 5/1973 France ............................... 548/246

OTHER PUBLICATIONS

Chem. Abstracts Chem. Substance Index, 9th Collective Index, (1972–1976), p. 39193CS, (1978).
Chemical Abstracts, vol. 63, No. 6, Abstract No. 6999b, Sep. 13, 1965.
Chemical Abstracts, vol. 66, No. 22, Abstract No. 100194x, May 29, 1967.
Chemical Abstract, vol. 61, No. 3, Abstract No. 3094h, Aug. 3, 1964.

Primary Examiner—Mary C. Lee
Attorney, Agent, or Firm—Connolly and Hutz

[57] ABSTRACT

New hydroxyalkyl-1,2,4-triazolidine-3,5-diones corresponding to the general Formula I

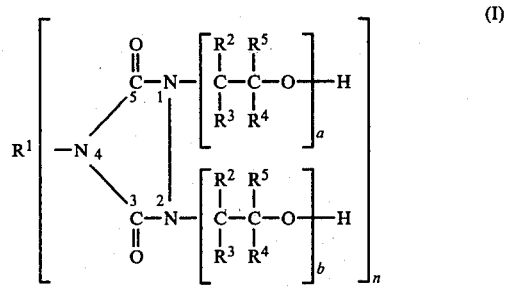

in which
 $R^1$ represents a monofunctional to pentafunctional organic radical, optionally substituted and/or optionally interrupted by hetero atoms or hetero atom groups,
 $R^2$, $R^3$, $R^4$ and $R^5$ are the same or different and represent hydrogen, an aliphatic $C_1$–$C_{10}$-radical, a cycloaliphatic $C_4$–$C_8$ radical or an araliphatic $C_7$–$C_{17}$-radical, said radicals are optionally substituted by halogen, an aromatic $C_6$–$C_{16}$-radical or an aromatic $C_6$–$C_{16}$-radical substituted by halogen, $C_1$–$C_4$-alkyl or $C_1$–$C_4$-alkoxy, a and b are the same or different and represent a number of from 1 to 30, and n=a number of from 1 to 5.

The new compounds are obtained by oxalkylation reaction using 1,2,4-triazolidine-3,5-diones of Formula I as starting materials in which a and b represent the number 0.

2 Claims, No Drawings

HYDROXYALKYL-1,2,4-TRIAZOLIDINE-3,5-DIONES AND A PROCESS FOR THEIR PRODUCTION

This invention relates to new hydroxyalkyl-1,2,4-triazolidine-3,5-diones corresponding to the following general formula (I):

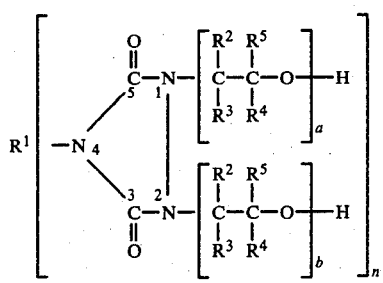

in which

R[1] represents a monofunctional to pentafunctional unsubstituted or substituted, linear or branched aliphatic $C_1$-$C_{30}$-, preferably $C_1$-$C_{12}$-radical, a monofunctional to pentafunctional unsubstituted or substituted cycloaliphatic $C_5$-$C_{21}$-radical, a monofunctional to pentafunctional unsubstituted or substituted aliphatic-aromatic $C_7$-$C_{17}$-, preferably $C_7$-$C_{10}$-radical, or a monofunctional to pentafunctional unsubstituted or substituted aromatic $C_6$-$C_{21}$-, preferably $C_6$-$C_{15}$-radical; the aliphatic radicals mentioned above may be interrupted by at least one oxygen atom or tertiary nitrogen atom, whilst the polynuclear cycloaliphatic, polynuclear aliphatic-aromatic and polynuclear aromatic radicals mentioned above may be interrupted by at least one oxygen or tertiary nitrogen atom or by at least one alkylene group containing from 1 to 4 carbon atoms or by at least one sulfonyl group $$(-\overset{O}{\underset{O}{\overset{\|}{S}}}-),$$

R[2], R[3], R[4] and R[5] may be the same or different and represent hydrogen, an aliphatic $C_1$-$C_{10}$-radical, a halogen (chlorine, bromine)-substituted $C_1$-$C_{10}$ aliphatic radical, a cycloaliphatic $C_4$-$C_8$ or araliphatic $C_7$-$C_{17}$ radical, an aromatic $C_6$-$C_{16}$ radical or an aromatic $C_6$-$C_{16}$ radical substituted by halogen (chlorine, bromine), $C_1$-$C_4$-alkyl or $C_1$-$C_4$-alkoxy, a and b are the same or different and represent a number of from 1 to 30, and n is a number of from 1 to 5, preferably from 1 to 3.

Preferably, R[1] is unsubstituted and R[2], R[3] and R[4] represent hydrogen and R[5] represents hydrogen, methyl, ethyl or phenyl; in particular R[2], R[3] and R[4] represent hydrogen and R[5] represents hydrogen and methyl, in addition a and b are each a number of from 1 to 12, more particularly the number 1.

Preferred radicals R[1] correspond for example to the following formulae:

(a) $C_tH_{2t+1}-$   $t = 1$ to 18

(b) $-(CH_2)_m-$   $m = 2$ to 12

(c) $-[CH_2-\underset{R^6}{\overset{|}{C}H}-O]_p-CH_2-\underset{R^6}{\overset{|}{C}H}-$   $R^6 = H, CH_3$  $p = 1-9$ (d) $-[CH_2(CH_2)_q-\underset{R^7}{\overset{|}{N}}-]_r-(CH_2)_q-CH_2-$   $R^7 = C_1$-$C_4$—alkyl  $q = 1-2$  $r = 1-4$ (e) ⌬—, ⌬—Cl (f) naphthyl—

(g) ⌬—CH$_2$—

(h) cyclohexyl (H)

(i) cyclohexenyl (H)

(j) $H_3C\underset{H_3C}{\overset{H_3C}{\diagdown}}$cyclohexyl$-CH_2-$ (k) (H)—A—(H)   $A = C_1$-$C_4$—alkylene, O, $-N(CH_3)-$;

(l) 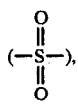

(m) $-CH_2$—⌬—$CH_2-$ (n) ⌬

(o) (⌬)—X—(⌬)   $X = C_1$-$C_4$—alkylene, O, $-N(CH_3)-$;

(p) ⌬—[CH$_2$—⌬—]$_{1\ to\ 3}$CH$_2$—⌬

(q) $C_4H_9-O-CH_2-CH_2-CH_2-$ (r) $-(CH_2)_3-O-(CH_2)_{\overline{2\ to\ 4}}O-(CH_2)_3-$ (s) 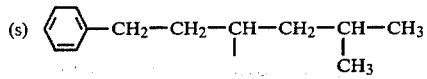

The starting triazolidine-3,5-diones required for producing the hydroxyalkyl-1,2,4-triazolidine-3,5-diones of formula (I) corresponding to the invention may be obtained by various processes.

Thus, amines corresponding to the following formula:

         (II)

in which $R^1$ and n have the same meaning as in formula (I), are reacted with hydrazodicarbonamide (process 1) or with 1,2,4-triazolidine-3,5-dione (process 2) at 150° to 280° C. in the presence or absence of a solvent, such a N-methyl pyrrolidone, or solvent mixture under pressures of from 50 mbar to 5 bars and optionally in the presence of an acid or basic catalyst, such as alcoholates or tertiary amines, with elimination of ammonia to form the starting 1,2,4-triazolidine,3,5-diones.

Another possible method of producing the starting 1,2,4-triazolidine,3-5-diones is to react N-monosubstituted hydrazodicarbonamides corresponding to the following formula:

         (III)

in which $R^1$ and n have the same meaning as in formula (I) under the same conditions as described above for processes 1 and 2 with elimination of ammonia to form the starting 1,2,4-triazolidine-3,5-diones. The N-monosubstituted hydrazodicarbonamides corresponding to formula (III) may be obtained by known methods from semicarbazide and isocyanates corresponding to formula (IV):

         (IV)

in which $R^1$ and n have the same meaning as in formula (I).

The hydroxyalkyl-1,2,4-triazolidine-3,5-diones of general formula (I) according to the invention are obtained by reacting 1,2,4-triazolidine-3,5-diones corresponding to the following formula (V):

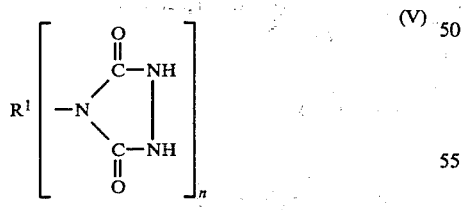         (V)

in which $R^1$ and n have the same meaning as in formula (I), with alkylene oxides, particularly ethylene oxide, propylene oxide and styrene oxide, optionally in the presence of a suitable catalyst.

Addition of the alkylene oxide with the NH-groups of the 1,2,4-triazolidine-3,5-diones of formula (V) may be carried out in the presence both of acid catalysts and of alkaline catalysts. However, in the production of polyols corresponding to formula (I), it is preferred to use basic catalysts, such as tetraethyl ammonium chloride, tertiary amines, such as triethyl amine and dimethyl aniline, and alkali or alkaline earth metal hydroxides or their carbonates, such as calcium hydroxide or potassium carbonate. However, alkali metal halides, such as lithium chloride, may also be used. The catalyst is generally used in a quantity of from 0.05 to 3%, based on the reactants.

One preferred embodiment is the addition of 1 mole of alkylene oxide per NH-group in the absence of a catalyst.

The polyhydroxy compounds corresponding to formula (I) are preferably produced using equivalent quantities, i.e. n (a+b) moles of alkylene oxide are used per mole of 1,2,4-triazolidine-3,5-dione of formula (V).

The reaction of the 1,2,4-triazolidine-3,5-diones corresponding to formula (V) with the alkylene oxide is preferably carried out in inert organic solvents. Particularly suitable inert organic solvents are polar organic solvents, such as dimethyl sulfoxide, tetramethylene sulfone, dimethyl formamide, dimethyl acetamide and N-methyl-2-pyrrolidone. Water is also a very suitable solvent. Surprisingly, the ethylene oxide does not react with the water. In this connection, it is not absolutely essential to react the 1,2,4-triazolidine-3,5-diones of formula (V) in solution with the alkylene oxide. The reaction may even be carried out in a suspension of the 1,2,4-triazolidine-3,5-dione of formula (V), in which case the polyol formed passes into solution so that the end of the reaction is indicated by the presence of a clear solution. 1,2,4-triazolidine-3,5-dione of formula (V) and alkylene oxide may also be introduced together into the polyol solution formed so that the quantity of solvent is kept very small. For economic reaons, the quantity of solvent should be very small and may amount to between 0.3 part by weight and 20 parts by weight of solvent per part by weight of reactants. On completion of the reaction, the solvent is removed by applying a vacuum and the viscous residue left is purified by standard methods, such as recrystallisation. In many cases, however, there is no need for purification and the crude product is immediately further processed.

The reaction is preferably carried out at temperatures in the range of from 25° C. to 200° C. and more preferably at temperatures in the range of from 80° C. to 150° C.

The reaction times are generally between 30 minutes and several days although, in special cases, they may even be shorter or longer. Shorter reaction times are obtained by suitably selecting the reaction conditions, for example the reaction pressure.

In one preferred embodiment, 1,2,4-triazolidine-3,5-diones of formula (V) are reacted with ethylene oxide in a lower dialkyl formamide (for example dimethyl formamide) at a temperature of 120° C. On completion of the reaction, the solvent is removed in a water jet vacuum and the reaction mixture is concentrated at 90°–100° C./0.2 mbar until constant in weight. The viscous residue formed frequently crystallises very quickly and, after suspension in methanol, ethanol, isopropanol, acetone or mixtures thereof, may be filtered off under suction. The almost pure poly-2-hydroxyethyl-1,2,4-triazolidine-3,5-diones of formula (I) obtained may be further purified by recrystallisation from the solutions mentioned above.

The hydroxyalkyl-1,2,4-triazolidine-3,5-diones produced in accordance with the invention may be incorporated as crosslinkers into known polyesters containing hydroxyl groups, for example of adipic acid, phthalic acid and diglycol, and are used for the production of rigid or flexible polyurethane foams.

The compounds of formula (I) corresponding to the invention, particularly where a and b=1, may be used as initiators in the production of polyethers containing hydroxyl groups which may in turn be used, depending on their molecular weight, for the production of rigid or flexible polyurethane foams.

The parts and percentages quoted in the Examples are based on weight unless otherwise indicated.

EXAMPLES

Production of the starting 1,2,4-triazolidine-3,5-diones corresponding to formula (V).

Starting Material 1

Sodium carbonate is added in small portions to a solution of 111.5 g of semicarbazide hydrochloride in 700 g of water until no more gas is given off. A solution of 119 g of phenyl isocyanate in 100 g of acetone is then added dropwise at 40° C. To complete the reaction, the reaction mixture is stirred for 2 hours at 40° C. and the deposit formed is isolated by filtration under suction.

The deposit, which is dried in air overnight, is suspended in 300 g of sulfolan and the resulting suspension is heated to 205° C., the ammonia given off being removed beyond 160° C. by applying a water jet vacuum of 420 mbars. After a reaction time of 5 hours, most of the solvent is removed under a pressure of 0.3 bars and the residue left is recrystallised from n-butanol. Filtration under suction and drying give 134 g of 4-phenyl-1,2,4-triazolidine-3,5-dione melting at 202° to 203° C. (lit. 203° C.).

Starting Material 2

600 g of hydrazodicarbonamide and 150 g of ethylene diamine are stirred in 500 ml of N-methyl pyrrolidone for 4 hours at 175° C. and for 20 hours at 200° C. A deposit is formed on cooling and is isolated by filtration under suction and washed with ethanol, giving 462 g (80% of the theoretical) of 1,2-ethanediyl-4,4'-bis-1,2,4-triazolidine-3,5-dione in the form of colourless crystals melting at 330° C.

|  |  | C | H | N |
|---|---|---|---|---|
| $C_6H_6N_6O_4$ | calculated | 31.58% | 3.53% | 36.83% |
| (228.2) | found | 31.4% | 3.6% | 36.8% |

IR (KBr): 1731, 1673 cm$^{-1}$ (C=O)

Starting Material 3

360 g of hydrazodicarbonamide, 807 g of stearyl amine and 1 ml of tin(II)dioctoate are stirred in 1 liter of N-methyl pyrrolidone for 4 hours at 175° C. and for 6 hours at 200° C. A deposit precipitates on cooling and is isolated by filtration under suction and washed with water, giving 955 g (90% of the theoretical) of 4-stearyl-1,2,4-triazolidine-3,5-dione in the form of colourless crystals melting at 118° to 120° C.

|  |  | C | H | N |
|---|---|---|---|---|
| $C_{20}H_{39}N_3O_2$ | calculated | 67.94% | 11.12% | 11.89% |
| (353.6) | found | 67.9% | 11.1% | 11.9% |

MS (m/e):mol. peak 353.

Starting Material 4

111.5 g of semicarbazide hydrochloride are dissolved in 250 ml of water and the resulting solution is neutralized with sodium carbonate. 169 g of 1-naphthyl isocyanate in 100 ml of dioxane are then added dropwise with vigorous stirring and cooling at room temperature. The mixture is then stirred for another hour at room temperature. The deposit formed is isolated by filtration under suction and washed with water.

The moist deposit is suspended in 1 liter of sulfolan and the resulting suspension is stirred at 150° C. until no more water distils off. The suspension is then stirred for 3 hours at 210° C./30 mbars. A deposit is formed on cooling and is isolated by filtration under suction and discarded. The mother liquor is concentrated in a high vacuum and the residue is extracted with 300 ml of 10% sodium hydroxide solution. Acidification of the alkaline solution with hydrochloric acid produces a deposit which is isolated by filtration under suction and washed with water, giving 123 g (54% of the theoretical) of 4-naphthyl-1,2,4-triazolidine-3,5-dione in the form of colourless crystals melting at 283° to 286° C.

|  |  | C | H | N |
|---|---|---|---|---|
| $C_{12}H_9N_3O_2$ | calculated | 63.43% | 3.99% | 18.50% |
| (227.2) | found | 63.5% | 3.9% | 18.7% |

$^1$HNMR($d_7$-DMF)=7.4–8.2 (m, 7H arom.) 10.43 ppm (s, 2H)

Starting Material 5

60 g of hydrazodicarbonamide and 29 g of 1,6-diaminohexane are stirred in 100 ml of sulfolan for 2 hours at 175° C. and for 9 hours at 200° C. A deposit precipitates on cooling and is isolated by filtration under suction and recrystallised from water, giving 36 g (51% of the theoretical) of 1,6-hexanediyl-4,4'-bis-1,2,4-triazolidine-3,5-dione in the form of colourless crystals melting at 215° to 217° C.

|  |  | C | H | N |
|---|---|---|---|---|
| $C_{10}H_{16}N_6O_4$ | calculated | 42.25% | 5.67% | 29.51% |
| (284.3) | found | 42.5% | 5.7% | 29.2% |

Starting Material 6

111.5 g of semicarbazide hydrochloride are dissolved in 400 ml of water and the resulting solution is neutralised with sodium carbonate. 57 g of methyl isocyanate dissolved in 300 ml of dioxane are then added dropwise with vigorous stirring over a period of 1 hour at room temperature. After stirring for another 2 hours at room temperature, the deposit formed is isolated by filtration under suction. The deposit is suspended in 1 liter of N-methyl pyrrolidone and the resulting suspension is pyrrolysed for 10 hours at 200° C./300 mbars. The solvent is then distilled off in vacuo and the residue is recrystallised from ethanol, giving 96 g (83% of the theoretical) of 4-methyl-1,2,4-triazolidine-3,5-dione in the form of colourless crystals melting at 230° to 232° C. (lit. 232°–233° C.).

Starting Material 7

102 g of 1,4-butane diol-bis-(3-aminopropyl ether) and 120 g of hydrazodicarbonamide are stirred in 300 ml of N-methyl pyrrolidone for 1 hour at 150° C., for 2 hours at 175° C. and for 5 hours at 200° C. A deposit precipitates on cooling and is isolated by filtration under suction and thoroughly boiled with 200 ml of acetonitrile, leaving as residue 142 g (76% of the theoretical) of 1,4-butane diol-bis-[3-(3,5-dioxo-1,2,4-triazolidin-4-yl)-propyl ether] in the form of colourless crystals melting at 152° to 154° C.

|  |  | C | H | N |
|---|---|---|---|---|
| $C_{14}H_{24}N_6O_6$ | calculated | 45.15% | 6.50% | 22.57% |
| (372.4) | found | 45.2% | 6.6% | 22.6% |

IR (KBr): 1768, 1674 cm$^{-1}$ (C=O)

Starting Material 8

131 g of 3-butoxypropylamine and 120 g of hydrazodicarbonamide are stirred in 300 ml of N-methyl pyrrolidone for 1 hour at 150° C., for 2 hours at 175° C. and for 6 hours at 200° C. A deposit precipitates on cooling and is isolated by filtration under suction and recrystallised from cyclohexane, giving 152 g (75% of the theoretical) of 3-(4-butoxypropyl)-1,2,4-triazolidine-3,5-dione in the form of colourless crystals melting at 83° to 85° C.

|  |  | C | H | N |
|---|---|---|---|---|
| $C_9H_{17}N_3O_3$ | calculated | 50.22% | 7.96% | 19.52% |
| (215.2) | found | 50.2% | 8.1% | 19.8% |

$^1$H-NMR(CDCl$_3$)=0.90 (t, 3H; J=6 Hz), 1.0-2.2 (m, 6H), 3.2-3.9 (m. 6H) 9.21 ppm (s, 2H).

Starting Material 9

191 g of 3-amine-5-methyl-1-phenylhexane and 120 g of hydrazocarbonamide are stirred in 250 ml of N-methyl pyrrolidone for 1 hour at 150° C., for 1 hour at 175° C. and for 2 hours at 200° C. A deposit precipitates on cooling and is isolated by filtration under suction and recrystallised from cyclohexane, giving 252 g (92% of the theoretical) of 4-(5-methyl-1-phenyl-3-hexyl)-1,2,4-triazolidine-3,5-dione in the form of colourless crystals melting at 114° to 115° C.

|  |  | C | H | N |
|---|---|---|---|---|
| $C_{15}H_{21}N_3O_3$ | calculated | 65.43% | 7.96% | 15.25% |
| (275.3) | found | 65.2% | 7.4% | 15.4% |

IR (KBr): 1767, 1671 cm$^{-1}$ (C=O)

Starting Material 10

101 g of 1,2,4-triazolidine-3,5-dione and 57 g of 1,4-diaminocyclohexane are heated with stirring in 500 ml of N-methyl pyrrolidone for 4 hours at 175° C. and for 30 hours at 200° C. A deposit crystallises out on cooling and is isolated by filtration under suction, washed with ethanol and dried, giving 110 g (78% of the theoretical) of 1,4-cyclohexanediyl-bis-(1,2,4-triazolidine-3,5-dione-4-yl) in the form of colourless crystals melting at >300° C.

|  |  | C | H | N |
|---|---|---|---|---|
| $C_{10}H_{14}N_6O_4$ | calculated | 42.56% | 4.96% | 29.75% |
| (282.2) | found | 42.7% | 5.1% | 29.1% |

MS (m/e): mol. peak 282

EXAMPLE 1

88 g of ethylene oxide are introduced into a solution of 177 g of 4-phenyl-1,2,4-triazolidine-3,5-dione (starting material 1) and 2.5 g of tetraethyl ammonium chloride in 100 g of dimethyl formamide over a period of 6.5 hours at 120° C. in such a way that no ethylene oxide escapes. The solvent is then distilled off in vacuo and the viscous residue is dissolved with heating in 250 ml of ethanol. A deposit precipitates on cooling and is isolated by filtration under suction and washed with ethanol, giving 199 g of 1,2-bis-(2-hydroxyethyl)-4-phenyl-1,2,4-triazolidine-3,5-dione in the form of colourless crystals melting at 133° C.

|  |  | C | H | N |
|---|---|---|---|---|
| $C_{12}H_{15}N_3O_4$ | calculated | 54.33% | 5.70% | 15.81% |
| (265.3) | found | 54.3% | 5.6% | 16.1% |

EXAMPLE 2

176 g of ethylene oxide are introduced into a suspension of 228 g of 1,2-ethanediyl-4,4'-bis-1,2,4-triazolidine-3,5-dione (starting material 2) and 2 g of triethyl amine over a period of 6 hours at 125° C. in such a way that no ethylene oxide escapes. Most of the solvent is removed by applying a vacuum of 40 mbar. The residue obtained (483 g) is dissolved with heating in 500 ml of a solvent mixture of 7 parts by volume of acetone and 3 parts by volume of isopropanol. A deposit precipitates on cooling and is isolated by filtration under suction and dried in vacuo, giving 330 g of 1,2-ethanediyl-4,4'-bis-[1,2-bis-(2-hydroxyethyl)-1,2,4-triazolidine-3,5-dione] in the form of colourless crystals melting at 153° to 155° C.

|  |  | C | H | N |
|---|---|---|---|---|
| $C_{14}H_{24}N_6O_8$ | calculated | 41.58% | 5.98% | 20.78% |
| (404.4) | found | 41.4% | 5.7% | 20.9% |

EXAMPLE 3

132 g of ethylene oxide are introduced into a melt of 530 g of 4-stearyl-1,2,4-triazolidine-3,5-dione (starting material 3) over a period of 6 hours at 120° C. in such a way that no ethylene oxide escapes. The reaction mixture is cooled and subsequently dissolved in 2.5 liters of acetone. A deposit precipitates on cooling and is isolated by filtration under suction and washed with acetone, giving 575 g of 1,2-bis-(2-hydroxyethyl)-4-stearyl-1,2,4-triazolidine-3,5-dione in the form of colourless crystals melting at 68° to 79° C.

|  |  | C | H | N |
|---|---|---|---|---|
| $C_{24}H_{47}N_3O_4$ | calculated | 65.27% | 10.73% | 9.52% |
| (441.7) | found | 65.6% | 10.7% | 9.4% |

EXAMPLE 4

8.8 g of ethylene oxide are introduced at 120° C. into 22.7 g of 4-(1-naphthyl)-1,2,4-triazolidine-3,5-dione (starting material 4) and 0.2 g of triethyl amine in 100 g of dimethyl formamide. On completion of the reaction, the solvent is distilled off in vacuo and the residue is dissolved with heating in isopropanol. A deposit precipitates on cooling and is isolated by filtration under suction and dried, giving 21 g of 1,2-bis-(2-hydroxyethyl)-4-(1-naphthyl)-1,2,4-triazolidine-3,5-dione melting at 211° to 212° C.

IR- and NMR-spectral together with elemental analysis confirm the assumed structure.

|  |  | C | H | N |
|---|---|---|---|---|
| $C_{16}H_{17}N_3O_4$ | calculated | 60.95% | 5.43% | 13.33% |
| (315.3) | found | 60.7% | 5.2% | 13.4% |

EXAMPLE 5

88 g of ethylene oxide are introduced into 142 g of 1,6-hexanediyl-4,4'-bis-1,2,4-triazolidine-3,5-dione (starting material 5) and 1 g of tetraethyl ammonium chloride in 250 g of dimethyl formamide over a period of 5 hours at 120° C. in such a way that no ethylene oxide escapes. Most of the solvent is removed by applying a vacuum of 50 mbars. The residue obtained (235 g) is dissolved with heating in a mixture of 300 ml of isopropanol and 500 ml of acetone. A deposit precipitates on cooling which is isolated by filtration under suction and dried in vacuo, giving 162 g of 1,6-hexanediyl-4,4'-bis-[1,2-bis-(2-hydroxyethyl)-1,2,4-triazolidine-3,5-dione] in the form of colourless crystals melting at 128° C. IR- and NMR-spectra together with elemental analysis confirm the assumed structure.

|  |  | C | H | N |
|---|---|---|---|---|
| $C_{18}H_{32}N_6O_8$ | calculated | 46.94% | 7.00% | 18.25% |
| (460.5) | found | 47.2% | 6.8% | 18.2% |

EXAMPLE 6

(a) 440 g of ethylene oxide are introduced into 575 g of 4-methyl-1,2,4-triazolidine-3,5-dione (starting material 6) and 5 g of lithium chloride in 1000 g of dimethyl formamide over a period of 8 hours at 110° to 120° C. in such a way that no ethylene oxide escapes. The solvent is distilled off by applying a vacuum. The residue is dissolved by heating in 1 liter of ethyl acetate. A deposit crystallises out on cooling and is isolated by filtration under suction and dried, giving 675 g of 1,2-bis-(2-hydroxyethyl)-4-methyl-1,2,4-triazolidine-3,5-dione melting at 126° to 127° C. (from ethanol). IR- and NMR-spectra together with elemental analysis confirm the assumed structure.

|  |  | C | H | N |
|---|---|---|---|---|
| $C_7H_{13}N_3O_4$ | calculated | 41.37% | 6.45% | 20.68% |
| (203.2) | found | 41.5% | 6.2% | 20.6% |

(b) 291 g of terephthalic acid dimethyl ester, 203 g of 1,2-bis-(2-hydroxyethyl)-4-methyl-1,2,4-triazolidine-3,5-dione from Example (6a), 31 g of 1,2-ethane diol and 92 g of glycerol are melted, and 1 g of lead acetate, 0.5 g of titanium tetrabutylate and 50 ml of xylene are added to the resulting melt, which is then heated for 8 hours at 200° C. After heating for 3 hours at 220° C., condensation is continued for 4 hours by applying a vacuum. 517 g of a brown resin which is brittle at room temperature are obtained. 30 g of this resin are dissolved in 70 g of a technical m-cresol, 0.9 g of a stabilised titanium tetrabutylate solution (prepared by heating 1 part by weight of titanium tetrabutylate and 2 parts by weight of cresol) is added to the resulting solution which is then applied to a degreased glass plate and stoved first for 20 minutes at 200° C. and then for 10 minutes at 300° C. An elastic film characterised by a smooth surface and a high softening temperature is obtained.

EXAMPLE 7

26.4 g of ethylene oxide are introduced at 110° C. into 55.8 g of 1,4-butane-bis-hydroxypropyl-3-diyl-[1,2,4-triazolidine-3,5-dione-4-yl] (starting material 7) and 0.3 g of trimethyl phenyl ammonium chloride in 100 g of dimethyl formamide. On completion of the reaction, the solvent is distilled off by applying a vacuum, leaving 85 g of a pale brown oil which for further purification is dissolved in a mixture of 7 parts by volume of chloroform and 3 parts by volume of methanol and filtered over silica gel. Removal of the solvent by distillation ultimately at 70° C./0.3 mbar leaves 75 g of a yellowish oil which consists mainly of 1,4-butane-bis-hydroxypropyl-3-diyl-[1,2-bis-(2-hydroxyethyl)-1,2,4-triazolidine-3,5-dione-4-yl]. IR- and NMR-spectra together with elemental analysis confirm the assumed structure.

|  |  | C | H | N | OH |
|---|---|---|---|---|---|
| $C_{22}H_{40}N_6O_{10}$ | calculated | 48.16% | 7.35% | 15.32% | 12.40% |
| (548.6) | found | 47.8% | 7.0% | 15.5% | 12.35% |

EXAMPLE 8

Following the procedure of Example 7, 53.75 g of 4-(3-butoxypropyl)-1,2,4-triazolidine-3,5-dione (starting material 8) are reacted with 22 g of ethylene oxide and the reaction product worked up, giving 69 g of a yellow oil consisting mainly of 1,2-bis-(2-hydroxyethyl-4-(3-butoxypropyl)-1,2,4-triazolidine-3,5-dione. IR- and NMR-spectra together with elemental analysis confirm the assumed structure.

|  |  | C | H | N | OH |
|---|---|---|---|---|---|
| $C_{13}H_{25}N_3O_5$ | calculated | 51.46% | 8.31% | 13.85% | 11.21% |
| (303.4) | found | 51.2% | 8.1% | 14.1% | 11.0% |

EXAMPLE 9

26.4 g of ethylene oxide are introduced into 82.5 g of 4-(5-methyl-1-phenyl-3-hexyl)-1,2,4-triazolidine-3,5-dione (starting material 9) and 0.3 g of trimethyl benzyl ammonium hydroxide in 150 g of dimethyl acetamide. The solvent is distilled off in vacuo, the residue is dissolved by heating in 150 ml of ethyl acetate, 10 g of powdered active carbon are added and the whole is filtered hot. A deposit crystallises out on cooling and is isolated by filtration under suction and dried, giving 68 g of 1,2-bis-(2-hydroxyethyl)-4-(5-methyl-1-phenyl-3-hexyl)-1,2,4-triazolidine-3,5-dione in the form of colourless crystals melting at 114° C. IR- and NMR-spectra together with elemental analysis confirm the assumed structure.

| | | C | H | N |
|---|---|---|---|---|
| $C_{19}H_{29}N_3O_4$ | calculated | 62.79% | 8.04% | 11.56% |
| (363.4) | found | 62.7% | 7.9% | 11.4% |

EXAMPLE 10

88 g of ethylene oxide are introduced at 120° C. into 141 g of 1,4-cyclohexanediyl-bis-(1,2,4-triazolidine-3,5-dione-4-yl) (starting material 10) and 0.5 g of triethyl amine in 250 g of dimethyl formamide. The solvent is distilled off in vacuo and the residue is dissolved by heating in 600 ml of ethyl acetate. A deposit crystallises out on cooling and is isolated by filtration under suction and dried, giving 174 g of 1,4-cyclohexanediyl-4,4'-bis-[1,2-bis-(2-hydroxyethyl)-1,2,4-triazolidine-3,5-dione] in the form of colourless crystals melting at 263° to 265° C. IR- and NMR-spectra together with elemental analysis confirm the assumed structure.

| | | C | H | N |
|---|---|---|---|---|
| $C_{18}H_{30}N_6O_8$ | calculated | 47.15% | 6.60% | 18.33% |
| (458.5) | found | 47.0% | 6.7% | 18.3% |

We claim:

1. A hydroxyalkyl-1,2,4-triazolidine-3,5-dione of the formula $$R^1 \left[ -N_4 \begin{array}{c} \overset{O}{\underset{5}{C}}-N_1-\begin{bmatrix} R^2 & R^5 \\ | & | \\ C-C-O \\ | & | \\ R^3 & R^4 \end{bmatrix}_a -H \\ \overset{3}{\underset{C}{\underset{\parallel}{C}}}-N_2-\begin{bmatrix} R^2 & R^5 \\ | & | \\ C-C-O \\ | & | \\ R^3 & R^4 \end{bmatrix}_b -H \end{array} \right]_n$$

wherein
$R^1$ is selected from the group consisting of $C_tH_{2t+1}-$ (a) wherein t is 1 to 18

$-(CH_2)_m-$ (b) wherein m is 2 to 12

$-[CH_2-\underset{R^6}{\overset{|}{CH}}-O]_p-CH_2-\underset{R^6}{\overset{|}{CH}}-$ (c) wherein $R^6$ is H or $CH_3$ and p is 1 to 9

$-[CH_2(CH_2)_q-\underset{R^7}{\overset{|}{N}}-]_r-(CH_2)_q-CH_2-$ (d) wherein $R^7$ is $C_1-C_4$—alkyl, q is 1 to 2 and r is 1 to 4

-continued phenyl- or Cl-phenyl- (e)

naphthyl- (f)

phenyl-$CH_2-$ (g)

cyclohexyl(H)- (h)

cyclohexyl(H)- (i)

2,2,6-trimethylcyclohexyl-$CH_2-$ (j)

bis(cyclohexyl)-A- (k) wherein A is $C_1-C_4$—alkylene, O or $-N(CH_3)-$ cyclohexyl-$CH_2-$ (l)

bis(cyclohexyl-$CH_2$)-$CH-$ (m)

$CH_2-phenyl-CH_2-$ (not shown label)

phenyl- (n)

bis(phenyl)-X- (o) wherein X is $C_1-C_4$—alkylene, O or $-N(CH_3)-$ phenyl-[$CH_2$-phenyl-]$_{1\ to\ 3}$-$CH_2$-phenyl- (p)

$C_4H_9-O-(CH_2)_3-$ (q)

$-(CH_2)_3-O-[CH_2]_{\overline{2\ to\ 4}}\ O-(CH_2)_3-$ and (r)

phenyl-$CH_2-CH_2-\underset{|}{CH}-CH_2-\underset{|}{CH}-CH_3$; (s)
 $\quad\quad\quad\quad\quad\quad\quad\quad\quad\quad\ \ \ CH_3$ $R^2$, $R^3$ and $R^4$ are hydrogen;
$R^5$ is hydrogen, methyl, ethyl or phenyl;
a and b are the same or different and represent a number of from 1 to 12 and
n is a number of from 1 to 5.

2. A hydroxyalkyl-1,2,4-trazolidine-3,5-dione as claimed in claim 1, wherein a and b represent the number 1.

* * * * *